United States Patent [19]

Wissmann et al.

[11] 4,426,325
[45] Jan. 17, 1984

[54] PROCESS FOR THE PREPARATION OF COMPOUNDS CONTAINING CARBOXYLIC ACID AMIDE GROUPS, IN PARTICULAR OR PEPTIDES

[75] Inventors: Hans Wissmann, Bad Soden am Taunus; Hans-Jerg Kleiner, Kronberg, both of Fed. Rep. of Germany

[73] Assignee: Hoechst Aktiengesellschaft, Frankfurt am Main, Fed. Rep. of Germany

[21] Appl. No.: 339,788

[22] Filed: Jan. 15, 1982

[30] Foreign Application Priority Data

Jan. 17, 1981 [DE] Fed. Rep. of Germany ....... 3101427

[51] Int. Cl.$^3$ ..................... C07C 103/52; C07F 9/02; C09F 5/00
[52] U.S. Cl. ...................... 260/112.5 R; 260/502.4 R; 564/140; 260/404; 564/138; 564/139; 564/141
[58] Field of Search ................. 260/112.5 R, 502.4 R, 260/404; 564/140, 138, 139, 141

[56] References Cited

U.S. PATENT DOCUMENTS

| | | | |
|---|---|---|---|
| 1,938,902 | 12/1933 | Grether et al. ..................... | 564/140 |
| 2,617,793 | 11/1952 | Young ............................ | 260/112.5 R |
| 2,617,794 | 11/1952 | Anderson ....................... | 260/112.5 R |
| 2,691,010 | 10/1954 | Anderson ....................... | 260/112.5 R |
| 2,708,667 | 5/1955 | Young et al. ................. | 260/112.5 R |
| 2,722,526 | 11/1955 | Anderson et al. ........... | 260/112.5 R |
| 2,722,539 | 11/1955 | Anderson ..................... | 260/112.5 R |
| 2,938,915 | 5/1960 | Schwyzer et al. ........... | 260/112.5 R |
| 3,630,875 | 12/1971 | Kuffer .......................... | 260/502.4 R |
| 4,331,592 | 5/1982 | Wissmann et al. ........... | 260/112.5 R |

FOREIGN PATENT DOCUMENTS 14834 3/1980 European Pat. Off. ..... 260/112.5 R

OTHER PUBLICATIONS

EGA–CHEMIC Catalogue, 1983, p. 1227.
J. Amer. Chem. Soc., vol. LXVIII, Jan.–Jul. 1946, pp. 539–542.
Tetrahedron Letters, No. 40, pp. 3627–3630, 1976. Pergamon Press, Great Britain.
Roberts, John D. and Marjorie C. Caserio, Basic Principles of Organic Chemistry, New York, 1965, pp. 1198–1200.
J. Zabicky, "The Chemistry of Amides" (1970) pp. 105–107.

Primary Examiner—Delbert R. Phillips
Attorney, Agent, or Firm—Curtis, Morris & Safford

[57] ABSTRACT

To prepare compounds containing carboxylic acid amide groups, in particular peptides, there are reacted compounds containing a carboxy group, in the presence of dialkylphosphinic acid anhydrides with compounds containing a free amino group.

4 Claims, No Drawings

PROCESS FOR THE PREPARATION OF COMPOUNDS CONTAINING CARBOXYLIC ACID AMIDE GROUPS, IN PARTICULAR OR PEPTIDES

A great number of processes for preparing carboxylic acid amide and peptide bonds has been proposed (cf., for example Houben-Weyl, Methoden per organischen Chemie, vol. XV, part II, pages 1–364; Angew. Chemie 92, 129 (1980). All of these processes aim at ensuring the characteristics which are required for the synthesis of peptides and have been more or less successful. Specifically, they should be free from racemization, be realizable in simple and gentle manner while giving high yields and while using easliy feasible, possibly harmless, starting products.

The present process provides a new method of optimizing said conditions for an economic synthesis of peptides and amides.

It has now been found that compounds containing carboxylic acid amide groups, in particular oligopeptides, can be prepared under gentle conditions in a high yield, by reacting compounds containing a free amino group, in particular aminocarboxylic acid derivatives or peptides, the carboxy groups of which are protected, in the presence of an anhydride of a dialkylphosphinic acid with compounds containing a free carboxy group, in particular aminocarboxylic acids or peptides, the amino group of which is acylated.

The radicals introduced to protect the functional group may be split off subsequently in usual manner, in the case of the synthesis of peptides.

By anhydrides of dialkylphosphinic acids there are to be understood compounds of the formula I

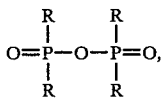

wherein R is alkyl. The substituents R may be identical or different. Anhydrides wherein both P atoms carry the same substituents are preferred.

Particularly appropriates for the present invention are anhydrides of the formula I wherein R is each time lower alkyl, preferably an alkyl having from 1 to 4 carbon atoms.

The dialkylphosphinic acid anhydrides used according to the present invention are colorless liquids. They are stable at room temperature and may be distilled under reduced pressure without being decomposed. They are readily soluble in most of the non-aqueous solvents, in particular lipid solvents such as chloroform or methylene chloride, but also in polar solvents such as dimethyl formamide and dimethyl acetamide.

Examples of suitable anhydrides of the dialkylphosphinic acids are: methylethylphosphinic acid anhydride, methylpropylphosphinic acid anhydride, methylbutylphosphinic acid anhydride, diethylphosphinic acid anhydride, di-n-propylphosphinic acid anhydride, di-n-butylphosphinic acid anhydride.

The dialkylphosphinic acid anhydrides may be prepared in known manner, for example by reacting dialkylphosphinic acid chlorides with dialkylphosphinic acid alkyl esters at 150°–160° C. (cf. Houben-Weyl, Methoden der Organischen Chemie, published by G. Thieme Verlag, Stuttgart 1963, vol. XII, pages 22 and follow.). Particularly preferred are processes wherein dialkylphosphinic acid, salts or esters thereof are reacted with phosgen (cf. German Pat. No. 2,129,583; German Offenlegungsschrift No. 2,225,545).

The reaction according to the present invention is carried out preferably in neutral or slightly alkaline medium. The most simple way of proceeding consists in adjusting the pH of the medium at the desired value by adding aliphatic or cycloaliphatic tertiary bases such as N-methylmorpholine, N-ethylmorpholine or trialkylamines having up to 6 carbon atoms in each alkyl group. When operating with systems consisting of water and a solvent miscible with water there may be used, instead of the organic base, alkali metal salts acting as buffer systems, for example salts of carbonic acid or of phosphoric acid.

Oligopeptides are prepared according to the process of the present invention by using as starting compounds on the one hand an amino acid or a peptide having a blocked carboxy group and on the other hand an amino acid or a peptide having a blocked amino group.

Any protective groups that are commonly applied in the peptide synthesis may be used for the protection of the carboxy groups. Particularly appropriate are esters of straight-chain or branched aliphatic alcohols such as methanol, ethanol, tertiary butanol. Esters of araliphatic alcohols such as benzyl alcohol or diphenylmethylcarbinol may be used alternatively.

Any protective groups that are usual in the peptide synthesis may be used likewise for the protection of the amino groups. Particularly appropriate are, for example, the carbobenzoxy radical and the carbo-tertiary butyloxy radical.

Suitable solvents are all anhydrous inert solvents that are commonly applied in the peptide synthesis, for example methylene chloride, chloroform, dimethyl formamide, dimethyl acetamide, dioxan or tetrahydrofuran.

The synthesis may be carried out alternatively using systems consisting of water and an organic solvent miscible with water such as dioxan/water, tetrahydrofuran/water or dimethyl formamide/water. Using such systems is particularly advantageous when connecting peptides that are predominantly water-soluble.

The reaction proceeds generally in sufficiently quick manner at room temperature. Slight heating is possible. Higher temperatures, however, for example of more than 50° C., are not recommended because of the danger of racemization, in particular in the peptide synthesis.

The dialkylphosphinic acid anhydrides according to the present invention are used preferably in excess (about 2 to 2.5 moles of dialkylphosphinic acid anhydride per mol of peptide bond to be bound). They may be added dropwise to the reaction mixture as auch in undiluted state.

The process according to the present invention is distinguished by a number of advantages, as compared to the actually common processes.

When using the dialkylphosphinic acid anhydrides there are left no difficulty soluble by-products upon completion of the synthesis, and the process of the invention is therefore superior over the peptide linkage forming processes using dicyclohexylcarbodiimide, which is frequently applied actually.

The dialkylphosphinic acid anhydrides are easier obtainable and easier to handle than most of the reagents commonly used for this purpose as far as they show little racemization.

As compared to the hitherto used processes for the peptide synthesis using activation agents based on trivalent or pentavalent phosphorus, for example the peptide synthesis by the phosphorus azo method (cf. Liebigs Ann. Chem. 580, page 68), synthesis methods using diethylchlorophosphite or tetraethylpyrophosphite (cf. J.Am. Chem. Soc. 74, 5304 (1952) and J. Am. Chem. Soc. 74, 5307 and 5309 (1952) and the synthesis method using polyphosphoric acid esters (cf. Ber. 91, (1958), p. 1073–1082), the process according to the present invention has the advantage of showing little racemization.

The process of the present invention can be carried out in simple manner and yields peptides in a high optical purity and in a high yields. It is moreover economical and little polluting.

The dialkylphosphinic acid anhydrides are of low molecular weight, they are easy to obtain and easy to purify and have a high portion of reactive groups, per weight unity, as well as a good lipophility. The dialkylphosphinic acid anhydrides and the corresponding dialkylphosphinic acids are lipid-soluble. This permits a working up of water-soluble peptide derivatives via a first precipitation step using suitable lipoid solvents.

The dialkylphosphinic acid obtained from the dialkylphosphinic acid anhydride in the course of the peptide synthesis may be recovered from the remaining solutions of the synthesis reaction.

The dialkylphosphinic acids may be recovered from a relatively great quantity of aqueous synthesis mother liquors by extracting with solvents such as chloroform and isobutanol, followed by distillative working up, it being of particular technical interest that the dialkylphosphinic acids can be distilled in vacuo without being decomposed The recovered dialkylphosphinic acids may be converted easily into the corresponding dialkylphosphinic acid anhydrides by the process of German Offenlegungsschrift No. 2,225,545.

When operating with the system consisting of water and an organic solvent miscible with water as described hereinbefore, the organic base may be replaced by salts of carbonic acid or phosphoric acid showing an alkaline reaction in aqueous solution, which facilitates the abovedescribed working up of the dialkylphosphinic acids following the synthesis. In this case the extraction step can be dispensed with. The dialkylphosphinic acid, upon liberation, can be directly separated by distillation from the evaporated mother liquor of the synthesis.

The present invention will be illustrated in the following examples.

EXAMPLE 1

Carbobenzoxyglycine ethyl ester:

At 0° C., 7.0 g (0.05 mol) of H-Gly-OC$_2$H$_5$.HCl, 15 ml of N-ethyl morpholine and 20 g of methylethylphosphinic acid anhydride were added successively to a solution of 10.5 g (0.05 mol) of carbobenzoxy-glycine in 20 ml DMF, while stirring and cooling thoroughly. The mixture was brought to room temperature, while stirring. After 16 hours of standing at room temperature the solvent was distilled off in vacuo, and the residue was dissolved in a mixture of 200 ml of ethyl acetate and 100 ml of a 5% potassium bisulfate solution. The ethyl acetate solution was washed twice with 100 ml each of saturated sodium bicarbonate solution, dried over sodium sulfate and evaporated in vacuo.

Yield: 12.0 g of Z-dipeptide ester having a melting point of 80° (80% of the th.).

EXAMPLE 2

Z-Val-Tyr(Bu$^t$)His-OCH$_3$

At 0° C., 30 mol of N-ethyl morpholine, 21.5 g of Z-Val-Tyr-(Bu$^t$)-OH and 20 g of methylethylenephosphinic acid anhydride were added successively, while stirring, to a suspension of 11.5 g of H-His-OCH$_3$.HCl in 100 ml of dimethyl formamide. The reaction solution which was practically clear after the exothermic reaction had been completed was allowed to stand overnight at room temperature, thereafter the solvents were evaporated in vacuo at room temperature, and a mixture of 100 ml of saturated NaHCO$_3$ solution and 200 ml of acetic acid ethyl ester was added to the solution. The crude product was introduced into the ethyl acetate phase, while shaking, which phase was washed with a small amount of water, dried over sodium sulfate and then brought to dryness in vacuo. The Z-tri-peptide ester remaining in the residue became solid upon digesting with diethyl ether.

Yield: 21 g, melting point 188° to 190° $[\alpha]_D = 8.2°$ (c=1, DMF). From the mother liquor there may be obtained another 2.5 g of the peptide by evaporating the solvent and recrystallizing the mixture from acetic acid ethyl ester/diethyl ether. Total yield: 76% of the theory.

EXAMPLE 3

Z-Pro-Ala-Lys-(Boc)-Phe-NH$_2$ 19.1 Grams of H-Lys(Boc)-Phe-NH$_2$.HCl (0.044 mol) were dissolved in 100 ml of dimethyl formamide, and at 0° C. 26 ml of N-ethyl morpholine, 16.0 g (0.005 mol) of Z-Pro-Ala-OH and 17.5 g of methylethylphosphinic acid anhydride were added, while stirring. The reaction mixture was allowed to stand at room temperature for 48 hours, thereafter it was brought to dryness in vacuo, the residue was digested with 100 ml of 2 N sodium carbonate solution, 100 ml of a 10% aqueous citric acid solution and 100 ml of dist. water and was then dried in vacuo over phosphorus pentoxide.

Yield: 30.4 g=89% of the th. $[\alpha]_D = 27.0°$ (c=1, DMF); melt. point 163° C.

EXAMPLE 4

Z-Asp(OBu$^t$)-Phe-NH$_2$

At 0° C., 1.6 g (0.01 mol) of H-Phe-NH$_2$ were dissolved, together with 28 ml of N-ethyl morpholine in 20 ml of dimethyl formamide. While stirring and cooling, 3.23 g (0.01 mol) of Z-Asp(OBu$^t$)OH and 4 g. of methylethylphosphinic acid anhydride were added to said solution. The reaction solution thus prepared was allowed to stand overnight at room temperature. The product was worked up by extraction with ethyl acetate, washing with water, aqueous sodium bicarbonate solution and with a 5% aqueous KHSO$_4$ solution, by concentrating the ethyl acetate solution dried over sodium sulfate and by precipitating the final product with diethyl ether.

Yield: 4.0 g (85% of the th.), m.p. 162° $[\alpha]_D = -33.1°$ (c=1, CH$_3$OH)

EXAMPLE 5

Z-Gly-Thr(Bu$^t$)Phe-OCH$_3$ 18.6 Grams (0.05 mol) of H-Thr(Bu$^t$)-Phe-OCH$_3$.HCL, 30 ml (0.238 mol) of N-ethyl morpholine and 10.4 g (0.05 mol) of Z-Gly-OH were dissolved successively in 120 ml of dimethyl sulfoxide (p.a.

Merck), and 4 g of methylethylphosphinic acid anhydride were added portionwise, while stirring and cooling with ice and with the exclusion of moisture. Stirring was continued for another 24 hours at room temperature, and the reaction solution was then introduced into 500 ml of saturated sodium bicarbonate solution, whereupon the reaction product precipitated. The supernatant solution was decanted, and the precipitate was dissolved in acetic acid ethyl ester. The ethyl acetate solution was washed with water, dried over magnesium sulfate, largely concentrated in vacuo, and the final product was precipitated with petroleum ether. It crystalliued overnight at +4° C.

Yield: 18.0 g (75% of the theory); melting point: 95° C.; $[\alpha]_D = +26°$ (c=1, DMF).

EXAMPLE 6

Z-Phe-cyclohexylamide

30 Grams (0.01 mole) of Z-Phe-OH, 1.0 g (0.01 mol; 1.2 ml) of cyclohexylamine and 5 ml of N-ethyl morpholine were dissolved in 30 ml of DMF, and while cooling with ice and stirring, 4 g of methylethylphosphinic acid anhydride were added. When the exothermic reaction had been completed (with a rise in temperature of up to +10°), the solution was allowed to reach room temperature, while stirring, and the reaction mixture was then worked up as has been described in Example 1.

Yield: 3.3 g (85% of the th.) $[\alpha]_D = -2.8°$ (c=1, DMF) m.p. 167° C.

EXAMPLE 7

Z-Phe-Arg-Trp-Gly-OCH$_3$ 2.26 g (0.005 mol) of Z-Phe-Arg-OH and 1.55 g (0.005 mol) of H-Trp-Gly-OCH$_3$.HCl were dissolved in 10 ml of dimethyl formamide at 0° C. while adding 5 ml of N-ethyl morpholine. Next, 2 g of methylethylphosphinic acid anhydride were added dropwise while stirring at this temperature. Stirring was continued at room temperature for one hour, whereupon the batch was left to stand at room temperature for 20 hours. After separation of dimethyl formamide by distillation in vacuo at room temperature, the residue was digested with 30 ml of saturated sodium carbonate solution and the solids obtained were dried in vacuo over P$_2$O$_5$.

Yield: 3.0 g (90% of the theory). $[\alpha]_D = -28°$ (c=1, DMF).

EXAMPLE 8

H-Phe-Arg-Trp-Gly-OCH$_3$.2HCl

3 Grams of the carbobenzoxytetrapeptide were dissolved in 200 ml of methanol, the air in the reaction vessel was expelled by nitrogen and 1 g of a 10% Pd/barium sulfate catalyst was added. Hydrogenation was carried out in usual manner by stirring and passing through hydrogen. The pH of the reaction solution, determined by electrometric measurement, was maintained at 4.0 by adding a 1 N methanolic hydrochloric acid solution. The splitting off of the carbobenzoxy radical by hydrogenation was terminated after 2 and a half hours, which could be observed by the consumption of the 1 N methanolic HCl solution and by a stop of the CO$_2$ evaluation. Next, hydrogen was expelled from the reaction vessel by nitrogen, the solvents were suction-filtered from the catalyst under nitrogen, the solution was concentrated to dryness in vacuo at room temperature and the residue was digested with absolute diethyl ether.

Yield: Upon drying in a high vacuum: 2.5 g (practically quantitative). $[\alpha]_D = +5.5°$ (c=1, glacial acetic acid).

EXAMPLE 8a

Determination of the degree of racemization by high pressure liquid chromatography:

25 μl of a 0.4% solution of the peptide derivative of Example 8 were introduced into the separating column of a liquid chromatograph (dimensions of the column: 0.4×25 cm, packing Spherosil ® XOA 600 Normatom ® 5 μm) which had been equilibrated with a solvent mixture consisting of chloroform/methanol/water/formic acid/ammonium formate (900:400:30:7:2.5) and the chromatogram was developed by pumping the above-described solvent through the column at a rate of 2 ml per minute under a pressure of 141 bar. The diastereomeric peptides separated on the column were determined quantitatively in the flow photometer, based on their absorption at 280 nm. The D-Arg diastereomer of the above prepared hydrochloride of the tetrapeptide ester was eluted under said conditions about 10 minutes after the column separation had started, the L-diastereomer appeared about 15 minutes later. The quantity of the D-Arg-diastereomer amounted to 2% of the hydrochloride of the tetrapeptide ester that had been introduced.

EXAMPLE 9

Z-Trp-Gly-OCH$_3$

At 0° C. there were added while stirring 6.5 ml of N-methyl morpholine to a mixture of 3.35 g (0.05 mol) of Z-Trp-OH and 1.25 g of H-Gly-OMe. Into the solution obtained there were added dropwise at the temperature specified, while stirring, 4 g of methylethylphosphinic acid anhydride. The mixture was allowed to stand at room temperature for 10 hours and the solvent was separated by distillation in vacuo at room temperature. The residue was taken up by a mixture of 25 ml of water and 70 ml of ethyl acetate, the ethyl acetate extract was separated and the aqueous solution was extracted twice using each time 10 ml of ethyl acetate. The combined ethyl acetate extracts were washed twice using each time 7 ml of water, a 5% potassium sulfate solution (until an acid reaction took place) and a saturated NaHCO$_3$ solution until a slightly alkaline reaction took place. Upon drying over magnesium sulfate and clearing with active carbon, the solvent was largely separated by distillation in vacuo and the residue was digested with diisopropyl ether.

Yield: Upon drying in vacuo over phosphorus pentoxide: 2.86 g=70% of the theory; colorless crystals. Melting point: 157° C. $[\alpha]_D = -12.5°$ (c=1, glacial acetic acid).

EXAMPLE 10

Z-Trp-Gly-OCH$_3$

To the suspension of 3.35 g (0.01 mol) of Z-Trp-OH and 1.25 g (0.01 mol) of H-Gly-OCH$_3$ in 15 ml of dimethyl formamide there were added portionwise altogether 7 ml of water and subsequently 5.1 g of a finely powdered sodium bicarbonate. The suspension was largely clarified by adding dropwise 4 ml of methylethyl phosphinic acid anhydride. A sample of the reaction solution diluted with water showed a neutral reaction. Upon heating to room temperature the solution was stirred overnight and the solvents were separated by distillation in a high vacuum at room temperature. The residue was taken up in a mixture of 25 ml of water and 70 ml of ethyl acetate, the ethyl acetate extract was separated and the aqueous phase was extracted twice using each time 10 ml of ethyl acetate. The combined ethyl acetate extracts were washed twice using each time 7 ml of water, a 5% potassium bisulfate solution (until an acid reaction took place) and a saturated sodium bicarbonate solution (until s slightly alkaline reaction took place). Upon drying over magnesium sulfate the ethyl acetate solution was largely separated by distillation in vacuo and the residue was digested with diisopropyl ether.

Yield upon drying in vacuo over $P_2O_5$: 3.0 g (73% of the theory). Melting point: 157° C. $[\alpha]_D = -12.9°$ (c=1, glacial acetic acid).

EXAMPLE 11

Z-Trp-Gly-OCH$_3$

To a mixture of 3.35 g (0.01 mol) of Z-Trp-OH, 1.25 g (0.01 mol) of H-Gly-OCH$_3$.HCl and 15 ml of dimethyl formamide there was added while stirring at 0° C. a solution of 7.0 g of $K_3PO_4.H_2O$ in 8 ml of water. While further stirring there were added dropwise 4.0 ml of methylethylphosphinic acid anhydride and the batch was subsequently allowed to heat to room temperature while stirring. After a 24 hours' stirring at room temperature the solvents were separated by distillation in vacuo at room temperature, the residue was taken up in a mixture of 25 ml of water and 80 ml of ethyl acetate, the water phase left was extracted a second time with 20 ml of ethyl acetate and the combined ethyl acetate extracts were shaken three times using each time 8 ml of a 5% potassium bisulfate solution and a saturated sodium bicarbonate solution. Upon drying the ethyl acetate solution with sodium sulfate, the product was isolated by evaporating the solvents and digesting the residue with a low-boiling petroleum ether (boiling point 40°–80° C.)

Yield upon drying in a high vacuum over $P_2O_5$: 3.0 g (73% of the theory), melting point: 157° C. $[\alpha]_D = -12.9°$ (c=2, glacial acetic acid).

What is claimed is:

1. A process for the preparation of compounds containing carboxylic acid amide groups, which comprises reacting compounds containing a carboxy group, in the presence of dialkylphosphinic acid anhydrides, with compounds containing a free amino group and splitting off radicals that may have been introduced to protect other functional groups.

2. The process of claim 1, which comprises carrying out the reaction in a medium consisting of water and an organic solvent miscible with water.

3. The process of claim 2, which comprises buffering the reaction medium with alkali metal salts of carbonic acid and/or phosphoric acid.

4. The process as defined in claim 1 wherein said compound containing a carboxylic acid amide group is a peptide.

* * * * *